United States Patent [19]

Rhee et al.

[11] Patent Number: 5,861,030

[45] Date of Patent: *Jan. 19, 1999

[54] BILEAFLET MECHANICAL HEART VALVE HAVING ARROWHEAD SLOT HINGE CONFIGURATION

[75] Inventors: Richard S. Rhee, Diamond Bar; George X. Guo, Dove Canyon; Seik Oh, Laguna Hills, all of Calif.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 821,478

[22] Filed: Mar. 21, 1997

Related U.S. Application Data

[63] Continuation of Ser. No. 511,663, Aug. 7, 1995, abandoned.

[51] Int. Cl.⁶ .................................................. A61F 2/24
[52] U.S. Cl. ........................................................ 623/2
[58] Field of Search ...................................... 623/2

[56] References Cited

U.S. PATENT DOCUMENTS

| | | |
|---|---|---|
| 4,178,639 | 12/1979 | Bakros . |
| 4,272,854 | 6/1981 | Bakros . |
| 4,276,658 | 7/1981 | Hanson et al. . |
| 4,328,592 | 5/1982 | Klawitter . |
| 4,363,142 | 12/1982 | Meyer . |
| 4,373,216 | 2/1983 | Klawitter . |
| 4,443,894 | 4/1984 | Klawitter . |
| 4,446,577 | 5/1984 | Meyer et al. . |
| 4,451,937 | 6/1984 | Klawitter . |
| 4,605,408 | 8/1986 | Carpentier ................. 623/2 |
| 4,676,789 | 6/1987 | Sorensen et al. .......... 623/2 |
| 4,692,165 | 9/1987 | Bakros ....................... 623/2 |
| 4,822,353 | 4/1989 | Bakros ....................... 623/2 |
| 4,863,458 | 9/1989 | Bakros ....................... 623/2 |
| 4,863,459 | 9/1989 | Olin ............................. 623/2 |
| 4,872,875 | 10/1989 | Hwang ....................... 623/2 |
| 4,888,010 | 12/1989 | Bakros ....................... 623/2 |
| 4,892,540 | 1/1990 | Vallana ...................... 623/2 |
| 4,923,465 | 5/1990 | Knoch et al. ............. 623/2 |
| 4,935,030 | 6/1990 | Alonso ...................... 623/2 |
| 4,995,881 | 2/1991 | Knotch et al. ........... 623/2 |
| 5,002,567 | 3/1991 | Bona et al. ............... 623/2 |

(List continued on next page.)

FOREIGN PATENT DOCUMENTS

| | | |
|---|---|---|
| 0050439 | 10/1981 | European Pat. Off. . |
| 0050971 | 5/1982 | European Pat. Off. ............ 623/2 |
| 0133608 | 2/1984 | European Pat. Off. . |
| 0176337 | 9/1985 | European Pat. Off. . |
| 300512A2 | 9/1985 | European Pat. Off. . |
| 0091746B1 | 6/1986 | European Pat. Off. . |
| 211576A | 2/1987 | European Pat. Off. . |
| 0289404 | 4/1988 | European Pat. Off. . |
| 0327790 | 12/1988 | European Pat. Off. . |
| 0327790 | 8/1989 | European Pat. Off. ............ 623/2 |
| 0541215A1 | 8/1992 | European Pat. Off. . |
| WO86/05383 | 9/1986 | WIPO . |
| WO 88/03475 | 5/1988 | WIPO . |
| WO 91/05524 | 5/1991 | WIPO . |
| WO 91/11973 | 8/1991 | WIPO . |
| WO9202197 | 2/1992 | WIPO . |
| WO 92/21305 | 12/1992 | WIPO . |

*Primary Examiner*—David H. Willse
*Attorney, Agent, or Firm*—Robert D. Buyan; Raymond Sun; Guy L. Cumberbatch

[57] ABSTRACT

A bileaflet mechanical cardiovascular valve having a generally annular valve body and two occluder leaflets mounted within the valve body such that the occluder leaflets will move back and forth between an open configuration wherein blood is permitted to flow through the annular valve body and a closed configuration wherein blood is prevented from flowing in at least one direction through the annular valve body. Slots formed in opposite ends of the occluder leaflets are mounted upon raised mounting members formed on the inner surface of the annular valve body to facilitate the opening and closing movement of the occluder leaflets.

47 Claims, 9 Drawing Sheets

U.S. PATENT DOCUMENTS

| | | |
|---|---|---|
| 5,061,278 | 10/1991 | Bicer ............................................. 623/2 |
| 5,078,738 | 1/1992 | Couetil . |
| 5,108,425 | 4/1992 | Hwang ......................................... 623/2 |
| 5,116,366 | 5/1992 | Hwang ......................................... 623/2 |
| 5,116,367 | 5/1992 | Hwang et al. ............................... 623/2 |
| 5,123,920 | 6/1992 | Bakros ......................................... 623/2 |
| 5,137,532 | 8/1992 | Bakros et al. ............................... 623/2 |
| 5,147,390 | 9/1992 | Campbell ..................................... 623/2 |
| 5,152,785 | 10/1992 | Bakros et al. ............................... 623/2 |
| 5,171,263 | 12/1992 | Boyer et al. ................................. 623/2 |
| 5,178,632 | 1/1993 | Hanson ........................................ 623/2 |
| 5,192,309 | 3/1993 | Stupka et al. ............................... 623/2 |
| 5,192,313 | 3/1993 | Budd et al. .................................. 623/2 |
| 5,197,980 | 3/1993 | Gorshkov et al. .......................... 623/2 |
| 5,376,111 | 12/1994 | Bokros et al. ............................... 623/2 |

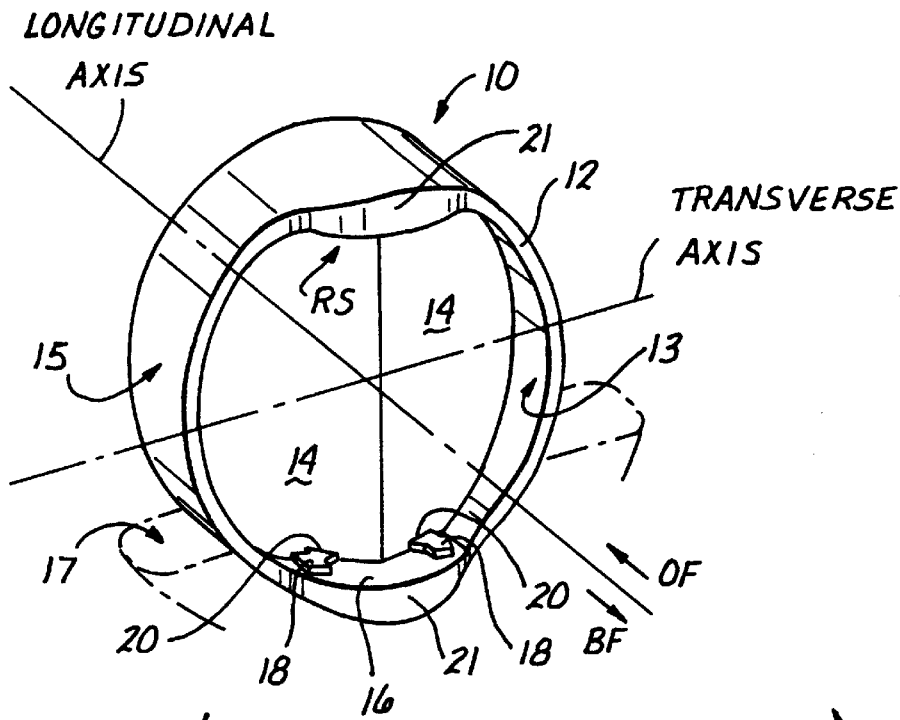
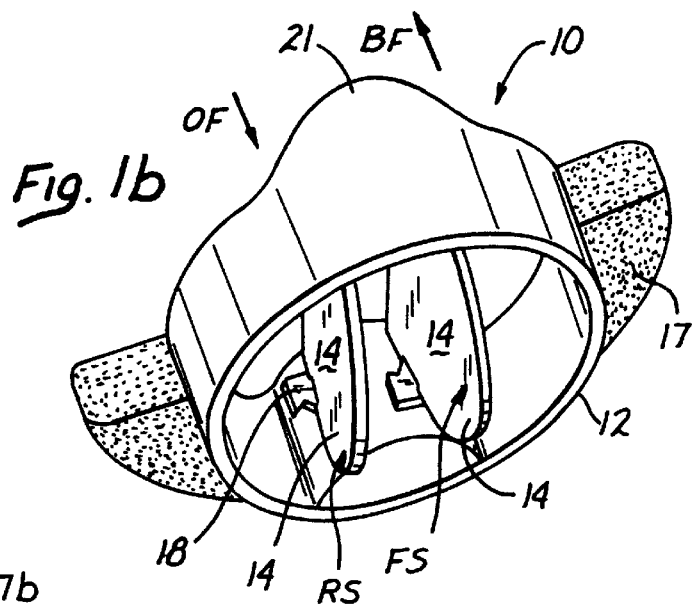
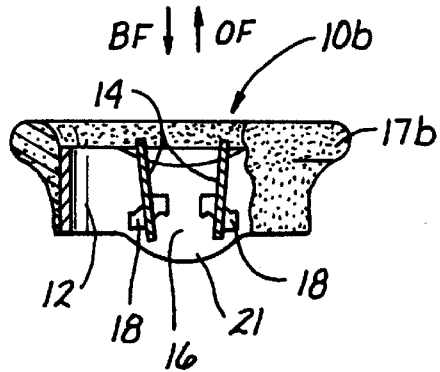
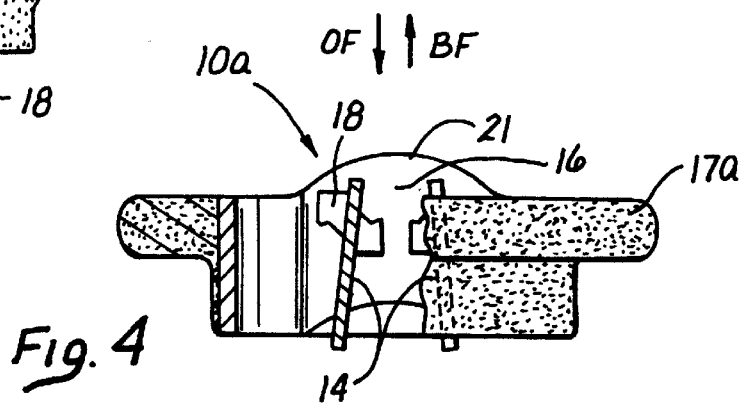

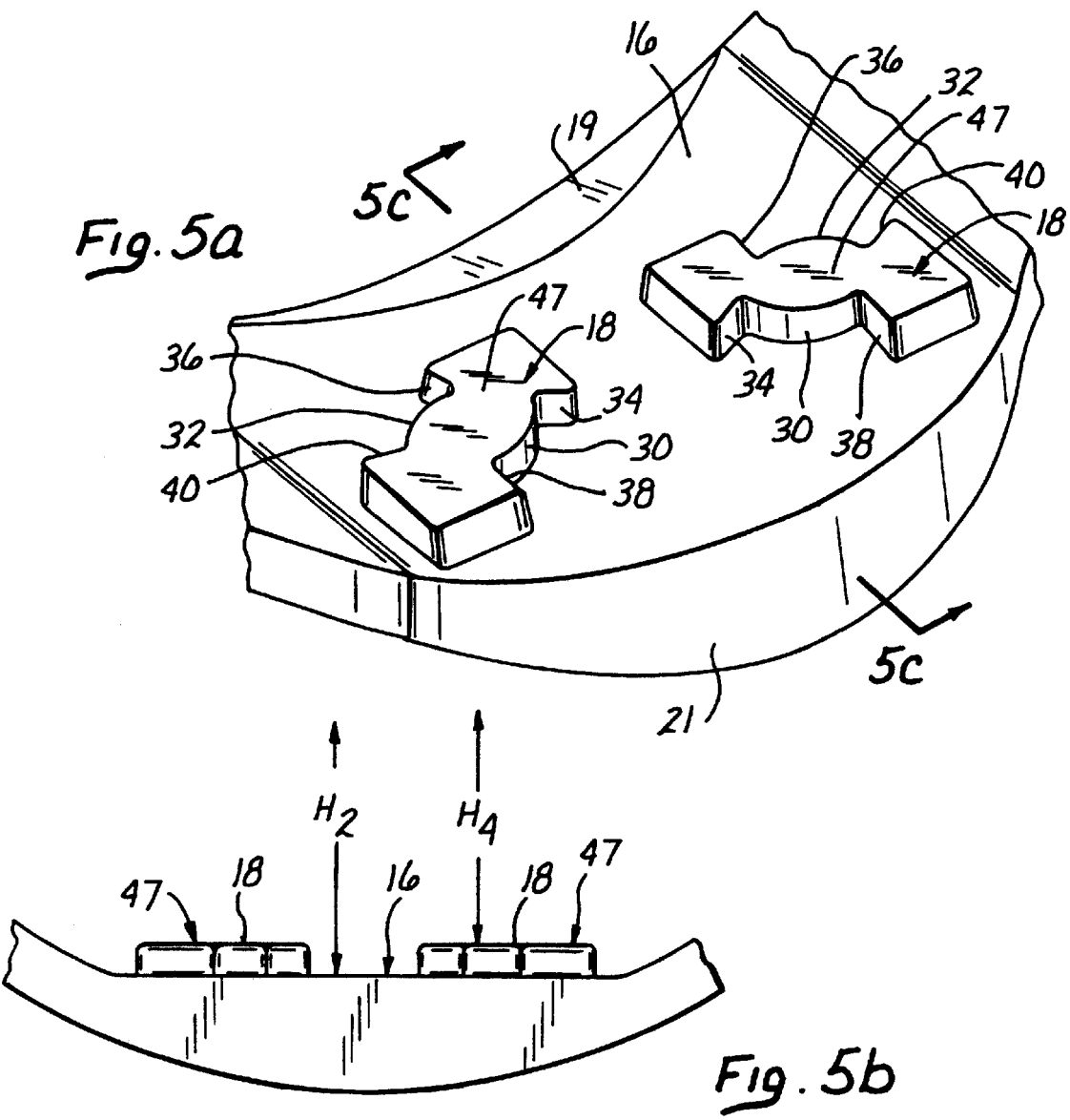
Fig. 5a
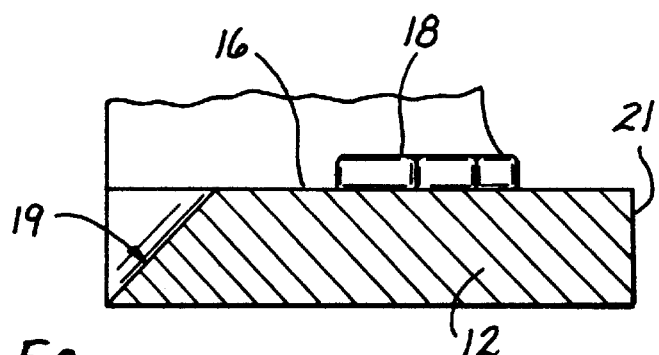
Fig. 5b
Fig. 5c

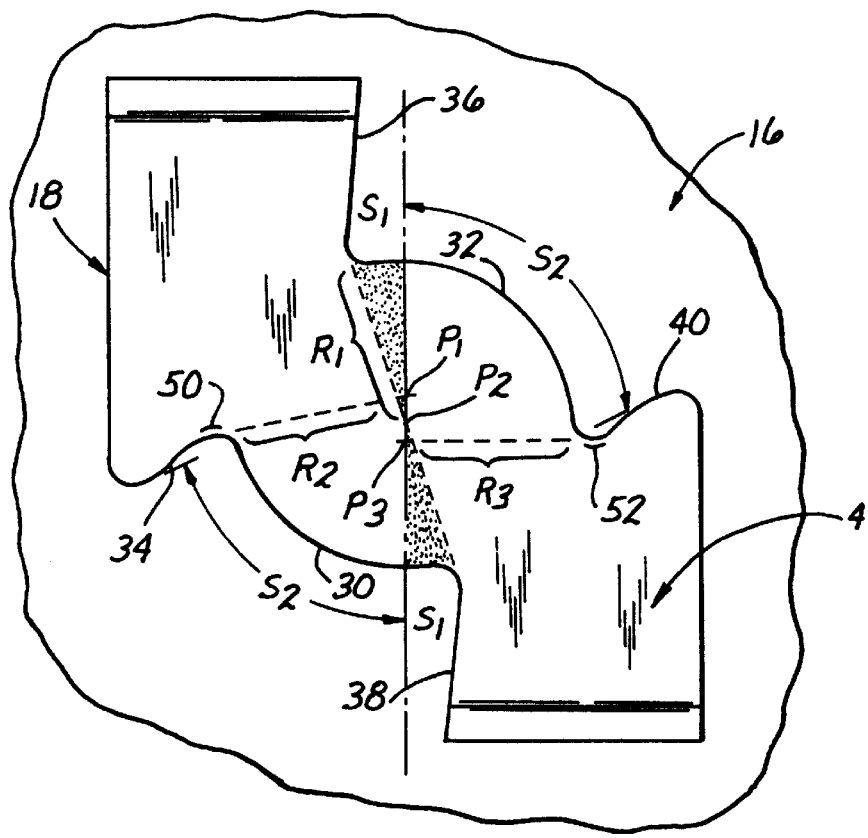
Fig. 6
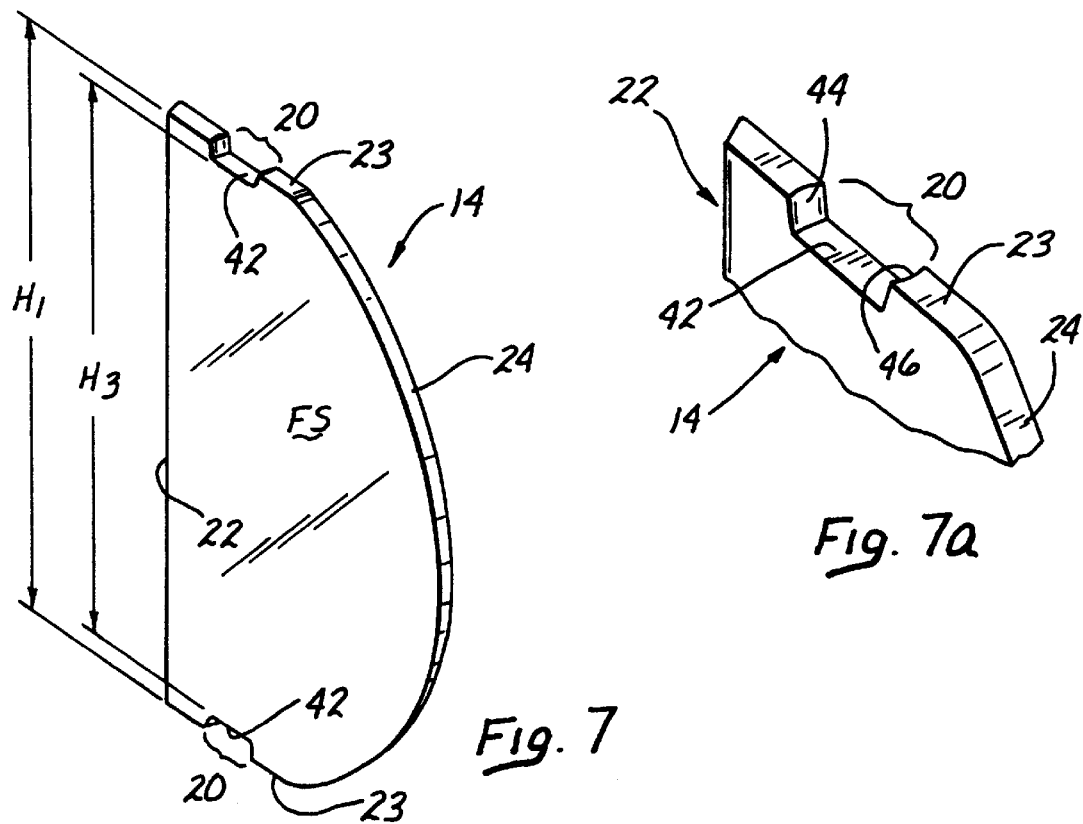
Fig. 7
Fig. 7a

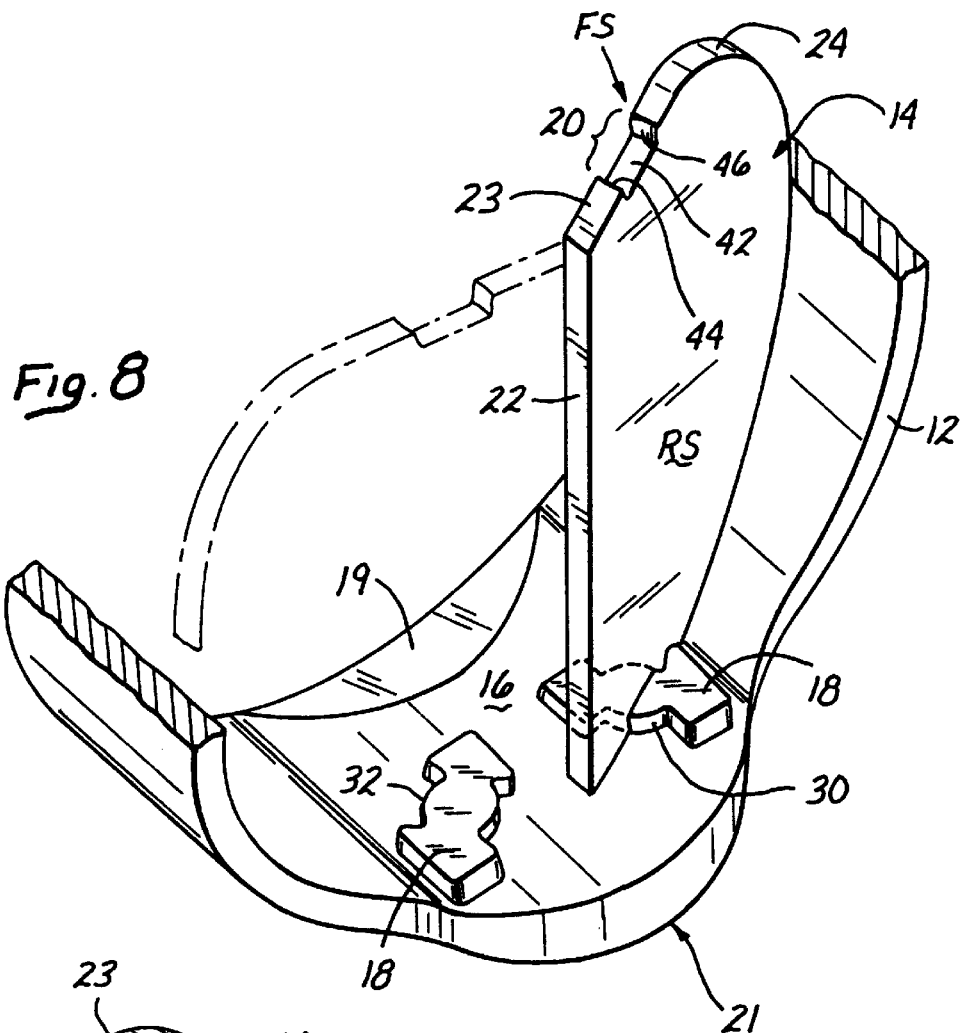
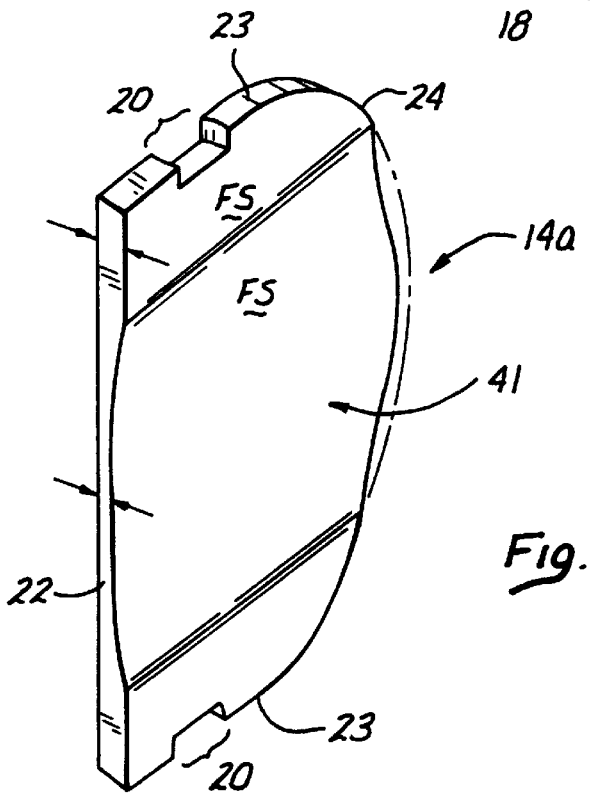

BILEAFLET MECHANICAL HEART VALVE HAVING ARROWHEAD SLOT HINGE CONFIGURATION

This is a continuation of application Ser. No. 08/511,663, filed on Aug. 7, 1995, now abandoned.

FIELD OF THE INVENTION

The invention pertains generally to medical devices and, more particularly, to a prosthetic mechanical cardiovascular valve.

BACKGROUND OF THE INVENTION

Many prosthetic mechanical heart valves have previously been used as surgically implantable replacements for malfunctioning endogenous anatomical heart valves.

One particular type of prosthetic mechanical heart valve is known as a "bileaflet" mechanical valve. Bileaflet type mechanical valves typically comprise a pair of flat occluder leaflets pivotally mounted within a ring-like annular valve body. The annular valve body is sutured into the heart (typically at the mitral or aortic position), as a replacement for a surgically removed endogenous valve. The occluder leaflets are pivotally mounted within the annular valve body such that the leaflets will move back and forth, in response to hemodynamic forces of the blood, between an "open" position whereby blood is permitted to flow through the annular valve body in a first direction, and a "closed" position whereby blood is prevented from backflowing in a second direction opposite said first direction.

In any prosthetic mechanical valve of the bileaflet type, it is desirable that the components of the valve be designed, configured and constructed so as to minimize or prevent stagnation or lodging of blood within the valve, as such stagnation or lodging of blood may give rise to thrombus formation and resultant thromboembolic complications. In bileaflet-type mechanical valves, one specific region where blood has been known to lodge or stagnate in crevices or notches formed as part of the hinge or pivot mechanism whereby the occluder leaflets are pivotally mounted within the annular valve body. In efforts to minimize such lodging or stagnation of blood, some of the bileaflet mechanical valves of the prior art have incorporated pivot/hinge mechanisms which are purportedly designed to perform a self-clearing or self-wiping function to dislodge blood which may tend to stagnate or lodge within the pivot/hinge mechanism of the valve.

Additionally, it is desirable that bileaflet mechanical prosthetic valves be designed so that the leaflets will open and close softly, without slamming or unnecessary surface-to-surface contact of a type likely to cause hemolysis (i.e., the breaking or rupture of blood cells).

Furthermore, it is desirable that heart valves of the bileaflet type be configured and constructed to withstand long term usage and wear, without fatigue, breakage or fracture of the valve components.

Examples of prosthetic mechanical heart valves of the prior art include those described in the following U.S. Pat. Nos.: 4,178,639 (Bokros), 4,272,854 (Bokros), 4,276,658 (Hanson, et al.), 4,328,592 (Klawitter), 4,363,142 (Meyer), 4,373,216 (Klawitter), 4,443,894 (Klawitter), 4,451,937 (Klawitter), 4,605,408 (Carpentier), 4,446,577 (Meyer, et al.), 4,676,789 (Sorensen, et al.), 4,692,165 (Bokros), 4,822,353 (Bokros), 4,863,458 (Bokros), 4,863,459 (Olin), 4,872,875 (Hwang), 4,888,010 (Bokros), 4,892,540 (Vallana), 4,923,465 (Knoch, et al.), 4,935,030 (Alonso), 4,995,881 (Knoch, et al.), 5,002,567 (Bona, et al.), 5,061,278 (Bicer), 5,078,738 (Couetil), 5,108,425 (Hwang), 5,116,366 (Hwang), 5,116,367 (Hwang, et al.), 5,123,920 (Bokros), 5,137,532 (Bokros, et al), 5,147,390 (Campbell), 5,152,785 (Bokros, et al.), 5,171,263 (Boyer, et al.), 5,178,632 (Hanson), 5,192,309 (Stupka, et al.), 5,192,313 (Budd, et al.), 5,197,980 (Gorshkov, et al.), as well as the following foreign patents and foreign patent publications: EP238181A, WO 86/05383, WO 91/11973, 0091746, 0465383A1, 0541215A1, WO 92/21305, 0023797, GB2055,452A, 0050439, GB2018396A, 0515324A1, WO92/02197, 0327790, EP289494, EP133608A, WO93/01767, EP89104A, EP256047A, EP436420A, EP 403649A, WO90/04367, EP176237A, and WO91/05524.

Although the prior art has included numerous surgically implantable bileaflet mechanical heart valves, there remains a need in the art for the development of new or improved bileaflet mechanical valves capable of long term, cardiac functioning with minimal likelihood of thromboembolic complications or other untoward side effects.

SUMMARY OF THE INVENTION

The present invention comprises a bileaflet mechanical cardiovascular valve comprising; an annular valve body having a central blood flow passageway extending therethrough and a pair of occluder leaflets mounted within said annular valve body. The occluder leaflets are mounted within the annular valve body by way of first and second pairs of leaflet mounting members formed at opposite locations on the inner surface of the annular valve body, and slots formed in the first and second ends of the occluder leaflets, each of said slots being configured to pivotally mount upon one of the leaflet mounting members. The occluder leaflets are alternately moveable between i) a closed position wherein the occluder leaflets block blood flow in at least a first direction through the annular valve body; and, ii) an open position wherein the occluder leaflets are substantially parallel to one another, and permit blood flow through the annular valve body in at least a second direction.

In accordance with the invention, each leaflet mounting member formed on the inner surface of the annular valve body may comprise a raised central body portion having first and second arcuate surfaces formed on opposite sides thereof, and flanking abutment surfaces which extend outwardly from, and are adjacent to, the ends of the first and second arcuate surfaces of the central body portion. The slots formed in the occluder leaflets are correspondingly configured such that each slot may be mounted over the central body portion of a corresponding leaflet mounting member, such that end surfaces of the slots will ride against the generally arcuate surfaces of the central body portions, and the flanking abutment surfaces will serve to limit or restrict the pivotal movement of the occluder leaflets as they reach their fully open and fully closed positions.

Still further in accordance with the invention, the occluder leaflets are preferably sized, relative to the annular valve body, such that gaps or spaces exist between the ends of the occluder leaflets and the adjacent inner surface of the annular valve body, when the occluder leaflets are in their closed positions. Blood is permitted to seep through such gaps or spaces, thereby performing a self-washing function to dislodge or remove any blood which may tend to lodge or become stagnated in the affected regions of the valve.

Still further in accordance with the invention, the flanking abutment surfaces of the leaflet mounting members against which the occluder leaflets abut when in their fully closed positions may be curved or otherwise configured such that, a space or gap will exist between that flanking abutment surface of the leaflet mounting member and the surface of the occluder leaflet which abuts thereagainst. Blood is thus permitted to seep through such gap or space, thereby performing a self-washing function to clear any blood which may tend to become lodged or stagnated in the affected regions of the valve.

Further objects and advantages of the invention will become apparent to those skilled in the art upon reading and understanding of the following detailed description and the accompanying drawings.

BRIEF DESCRIPTION OF THE DRAWINGS

FIG. 1a is a perspective view of a bileaflet mechanical heart valve of the present invention having its leaflets disposed in their closed positions.

FIG. 1b is a perspective view of a bileaflet mechanical heart valve of the present invention having its leaflets disposed in their opened positions.

FIG. 3 is an enlarged, partially sectional, elevational view of a bileaflet mechanical heart valve of the present invention sized and outfitted for implantation at the aortic position.

FIG. 4 is an enlarged, partially sectional, elevational view of a bileaflet mechanical heart valve of the present invention sized and outfitted for implantation at the mitral position.

FIG. 5a is an enlarged partial perspective view of the valve body of FIG. 5.

FIG. 5b is an enlarged partial elevational view of the annular valve body of FIG. 5.

FIG. 5c is an enlarged sectional view through line 5c—5c of FIG. 5a.

FIG. 6 is a plan view of a preferred leaflet mounting member formed on the inner surface of the annular valve body of a bileaflet mechanical valve of the present invention.

FIG. 7 is a perspective view of an occluder leaflet of a bileaflet mechanical cardiovascular valve of the present invention.

FIG. 7a is an enlarged perspective view of a portion of the occluder leaflet of FIG. 7.

FIG. 7b is a perspective view of an alternative configuration of an occluder leaflet of the present invention, wherein a concavity is formed in the mid-region of the leaflet to lessen the mass of the leaflet.

FIG. 8 is an enlarged, cut-away perspective view of a bileaflet mechanical cardiovascular valve of the present invention.

DETAILED DESCRIPTION OF THE PREFERRED EMBODIMENTS

Figure 2:
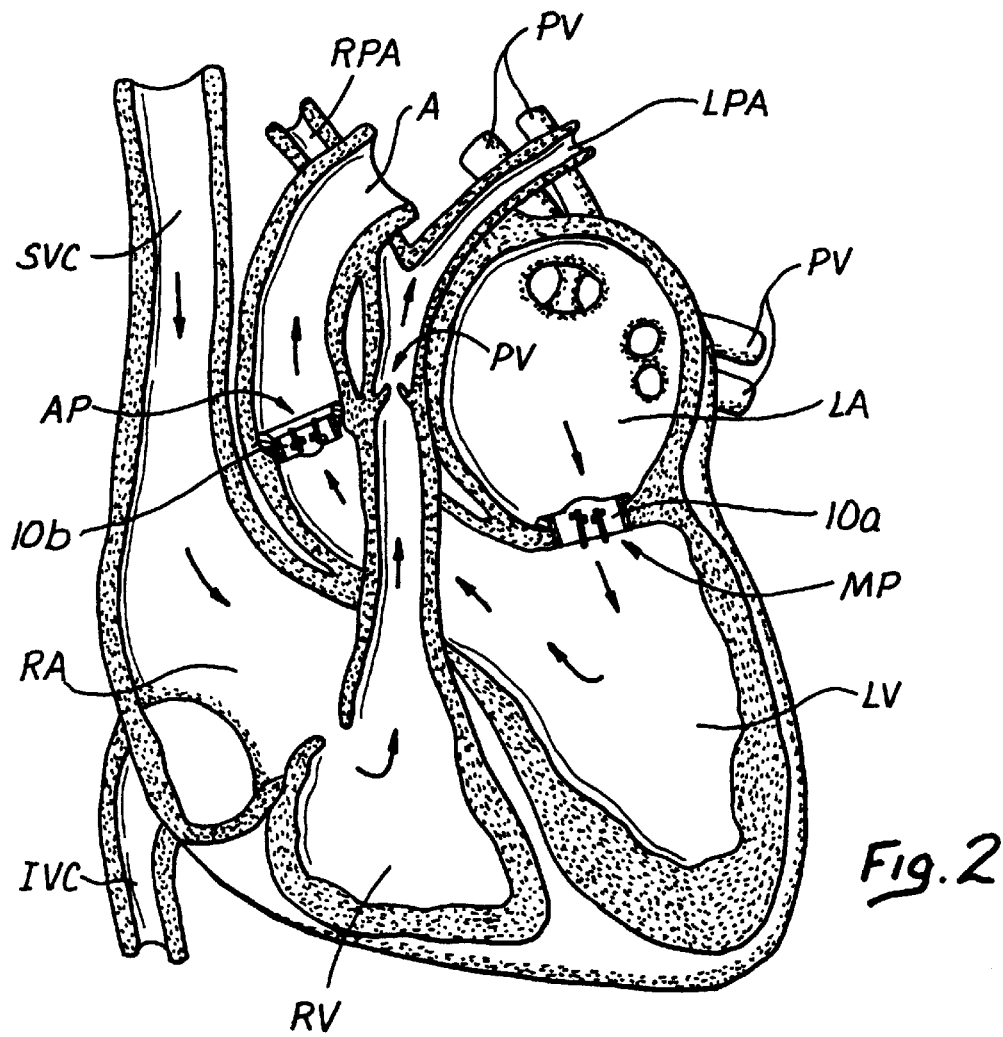
FIG. 2 is a cross-sectional of a human heart having bileaflet mechanical heart valves of the present invention implanted at the aortic and mitral positions therein.

The following detailed description and the accompanying drawings are provided for purposes of describing and illustrating presently preferred embodiments of the invention only and are not intended to limit the scope of the invention in any way.

A. General Structure And Assembly of Bileaflet Valve

As shown in the drawings, a presently preferred embodiment of the mechanical cardiovascular valve 10 of the present invention generally comprises an annular valve body 12 having a pair of occluder leaflets 14 pivotally mounted therein. The mounting of the occluder leaflets 14 within the annular valve body 12 is accomplished by the engagement and interaction of a plurality of leaflet-mounting members 18 formed on opposite sides of the inner surface of the annular body 12, with slots 20 formed on opposite ends of the occluder leaflets 14.

More specifically, the annular body 12 has an inner surface 13 and an outer surface 15. The inner surface 13 of the annular body 12 defines a central bore or blood flow passageway which extends longitudinally through the annular body 12. Upper and lower flat regions 16 are formed directly opposite one another on the inner surface 13 of the annular body 12. Right and left leaflet-mounting members 18 are formed on the upper and lower flat regions 16, as shown. The occluder leaflets 14 are snap-fit or otherwise positioned within the annular valve body 12 such that the slots 20 on the opposite ends of the occluder leaflets 14 are positioned on, and articulable with, the leaflet-mounting members 18. The specific interaction and articulation of the slots 20 with the leaflet-mounting members 18 will be described in more detail herebelow.

Each occluder leaflet 14 may comprise a substantially flat, planar leaflet body of substantially uniform thickness, as shown in FIG. 7. Alternatively, when it is desirable to decrease the mass of the leaflet, a concavity 41 may be formed in the mid-region of the leaflet 14a, as shown in the alternative embodiment of FIG. 7b. In either embodiment the leaflet 14, 14a has a frontal surface FS, a rear surface RS, an arched outer edge 24, a straight inner edge 22 and straight end edges 23. The outer edge 24 and inner edge 22 of each leaflet are beveled in opposite directions, as shown. Such beveling of the outer edge 24 and inner edge 22 facilitates seating of the leaflets in their desired closed positions, as will be more fully described herein.

Slots 20 formed in the opposite straight end edges 23 of the leaflets 14 are snap-fit onto, and engage with, the leaflet-mounting members 18. When the occluder leaflets 14 are in their closed positions, as shown in FIGS. 1a and 8, the front surfaces FS of the occluder leaflets 14 are disposed such that they form an acute angle, preferably of 120°–140°, relative to one another. Also, when the leaflets are in their closed positions the beveled inner edges 22 of the leaflets are in direct abutment with each other and the beveled arcuate outer edges 24 of the occluder leaflets 14 abut against the inner surface 13 of the annular valve body 12, as shown. Thus, when the occluder leaflets 14 are in their closed positions, they block the central bore of the annular valve body 12 in a manner which prevents regurgitation or backflow of blood through the central bore, in the direction labeled on the drawings as the backflow BF direction.

When the occluder leaflets 14 have pivoted to their open positions, as shown in FIG. 1b, the rear surfaces RS of the occluder leaflets 14 are directly opposite one another, and form an acute angle, preferably of 6°–16°, relative to each other. Thus, when in their open positions, the occluder leaflets 14 present minimal obstruction to flow and will cause minimal frictional drag on the flowing blood as it passes through the central bore of the annular valve body 12 in the outflow direction OF.

Although the bileaflet mechanical cardiovascular valve 10 of the present invention has numerous potential applications, and may be implanted at any suitable cardiac or extracardiac site, it will be appreciated that the primary sites for implantation of the valve 10 will be the intracardiac aortic position AP and mitral position MP as shown in FIG. 2.

The blood vessels and cardiac anatomical structures shown in FIG. 2 are labeled in accordance with the following legend:

PV . . . Pulmonary Veins
PA . . . Pulmonary Artery
RPA . . . Right Pulmonary Artery
LPA . . . Left Pulmonary Artery
SVC . . . Superior Vena Cava
IVC . . . Inferior Vena Cava
A . . . Aorta
RA . . . Right Atrium
RV . . . Right Ventricle
LA . . . Left Atrium
LV . . . Left Ventricle
AP . . . Aortic Valve Position
MP . . . Mitral Valve Position It will be appreciated that the mitral valve 10a and aortic valve 10b, of the present invention, differ in size, and are outfitted with suture rings 17 of differing configuration. These suture rings 17 are typically formed of Dacron or other needle-penetrable material, to facilitate suturing of the prosthetic valve to the host tissue. The suture rings 17a, 17b are specifically configured to facilitate suturing of the mitral valve 10a or aortic valve 10b of the present invention into the mitral position MP or aortic position AP of the heart, as shown in FIG. 2.

B. Preferred Configuration Leaflet Mounting Members

Figure 5:
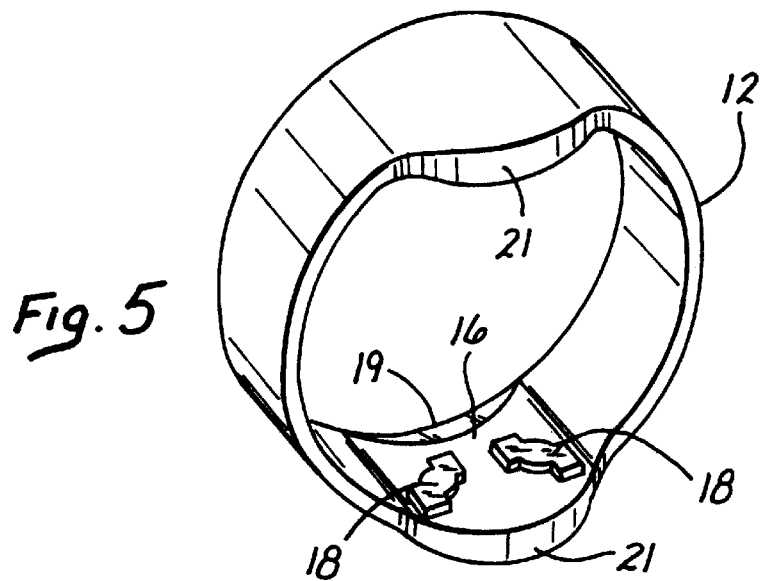
FIG. 5 is a perspective view of the annular valve body of a bileaflet mechanical heart valve of the present invention.

With particular reference to FIGS. 5–6, each leaflet mounting member 18 comprises a raised mass of matter which emanates or extends upwardly from a flat surface 16 of the annular valve body 12. Each leaflet-mounting member 18 has a generally flat top surface 47 and comprises a central body portion having a first generally arcuate edge surface 30 on one side thereof and a second generally arcuate edge surface 32 on an opposite side thereof. First flanking abutment surfaces 34, 40 extend outwardly from, and are positioned adjacent to, the first ends of the first and second generally arcuate edge surfaces 30, 32. Second flanking abutment surfaces 36, 38 extend outwardly from, and are positioned adjacent to, the second ends of the first and second generally arcuate edge surfaces 30, 32.

In the preferred embodiment, the first flanking abutment surfaces 34, 40 are preferably of curved configuration such that when the flat front or rear surface of a leaflet 14 abuts thereagainst, a gap or space 50, 52 will exist through which a small amount of blood may seep. Such seepage of blood between the front surface FS or rear surface RS of the leaflet and the adjacent first flanking abutment surface 34, 40 of the leaflet mounting member serves to dislodge any adherent or stagnating blood, as will be described more fully herebelow in relation to the operation of the valve components. In the specific configuration shown in the drawings, the first flanking abutment surfaces have radially arched indentations immediately adjacent the end of the first or second arcuate edge surface 30, 32. Such radially arched indentations preferably have radii of 0.02–0.025 inches each, and serve to provide the desired gap or space 50, 52 when the respective front surface FS or rear surface RS of the leaflet 14 is in abutment with the remaining flat portion of each first flanking abutments surface 34, 40. This aspect of the invention is specifically shown in FIGS. 11c and 11c', and is further described herein in relation to such figures.

Also, in the preferred embodiment, each of the first and second generally arcuate edge surfaces 30, 32 incorporates two (2) discreet arcuate segments $S_1$ and $S_2$. In this regard, the first arcuate segments $S_1$ of the first and second generally arcuate edge surfaces 30, 32 are positioned directly opposite one another, and share a common radius $R_1$ and a common mid-point $P_2$. The second arcuate segment $S_2$ of the first generally arcuate edge surface 30 has a radius $R_2$ and a center point $P_1$. The second arcuate segment $S_2$ of the second generally arcuate edge surface 32 has a radius $R_3$ and a center point $P_3$. In the embodiment shown, the radius $R_3$ of the second arcuate segment $S_2$ of the second generally arcuate edge surface 32 is equal to the radius $R_2$ of the second arcuate segment $S_2$ of the first generally arcuate edge surface 30.

C. Preferred Configuration of the Leaflet Mounting Slots

The slots 20 formed in the opposite straight end edges 21 of the leaflets 14 are configured to receive and articulate with the central body portions of the leaflet mounting members 18. In the embodiment shown, each slot 20 is defined by a flat inner surface 42 which is substantially parallel to the straight end edge 21, and radially curved end surfaces 44, 46. The radially curved end surfaces 44, 46 are configured to ride in abutment with the generally arcuate edge surfaces 30, 32 of the opposite sides of the central body portion of each leaflet mounting member 18. It will be appreciated that various alternative configurations of the slots 20 may also be employed, and that the end surfaces 44, 46 need not necessarily be of radially curved configuration, and may be of various straight or multi-sided configurations.

The occluder leaflets 14 are snap-fit into the annular valve body 12 such that each slot 20 is mounted over the generally round central body portion of a leaflet-mounting member 18 such that the first curved or radiused end surface 44 of each slot 20 is in juxtaposition to the first arcuate surface 30 of the leaflet-mounting member 18 and the second curved or radiused end 46 of slot 20 is juxtapositioned to the second arcuate surface 32 of leaflet-mounting member 18. The flat inner surface 42 of the slot 20 is in juxtaposition to the flat top surface 47 of the generally round central portion of the leaflet-mounting member 18.

D. Preferred Mounting of Valve Leaflets to Permit Floating of the Leaflets With Minimal Obstruction to Blood Flow The leaflets 14 are preferably sized and configured to allow the leaflets to move or "float" within the annular valve body. Also, the leaflets 14 are preferably sized and configured such that they may repeatedly open and close without frictional contact between the flat end edges 23 of the leaflets 14 and the adjacent flat surfaces 16 of the annular valve body 12. In this regard, if the annular valve body 12 is oriented such that one flat surface 16 is at the top and the other flat surface 16 is at the bottom, the leaflets 14 are sized, relative to the annular valve body 12, such that the leaflets may move or float up and down between an upper float limit and a lower float limit. The upper float limit is reached when the flat inner surfaces 42 of the slots 20 formed at the upper ends of the leaflets 14 come into contact with the flat top surfaces 47 of the mounting members 18 formed on the upper flat surface 16 of the annular valve body. The lower float limit is reached when the flat inner surface 42 of the slots 20 formed at the bottom ends of the leaflets 14 come into contact with the flat top surfaces 47 of the mounting members 18 formed on the bottom flat surface 16 of the annular valve body.

Figure 9A:
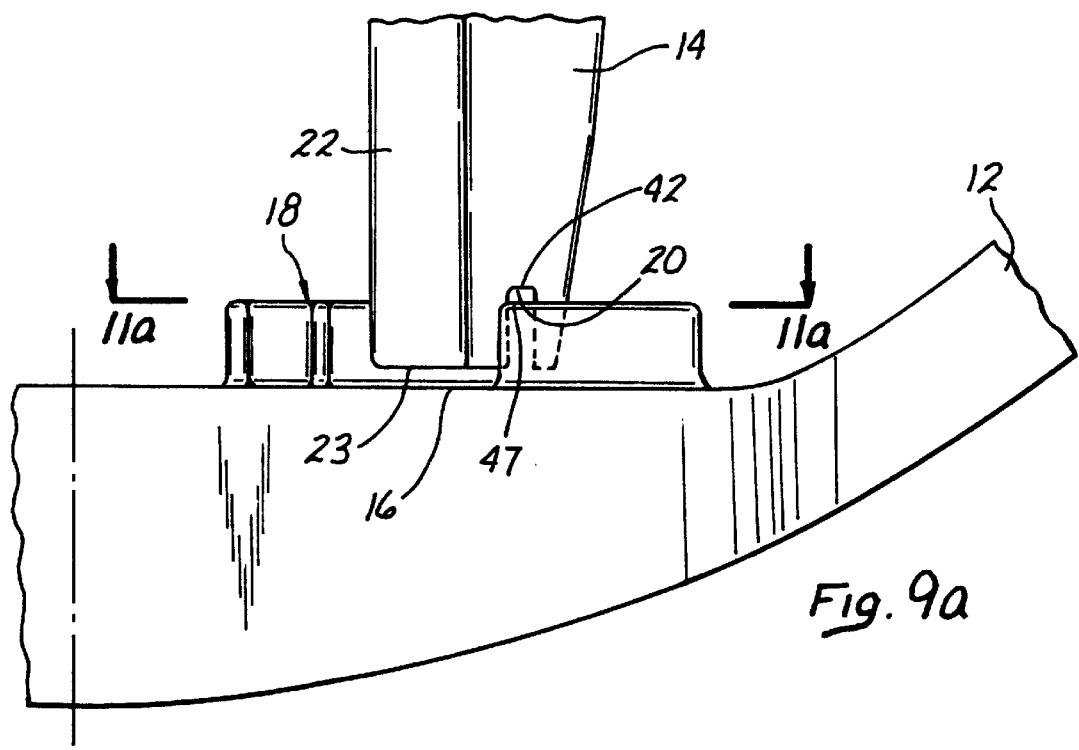
FIG. 9a is a partial elevational view of a bileaflet mechanical cardiovascular valve of the present invention with the occluder leaflet positioned in its fully opened position.
Figure 9B:
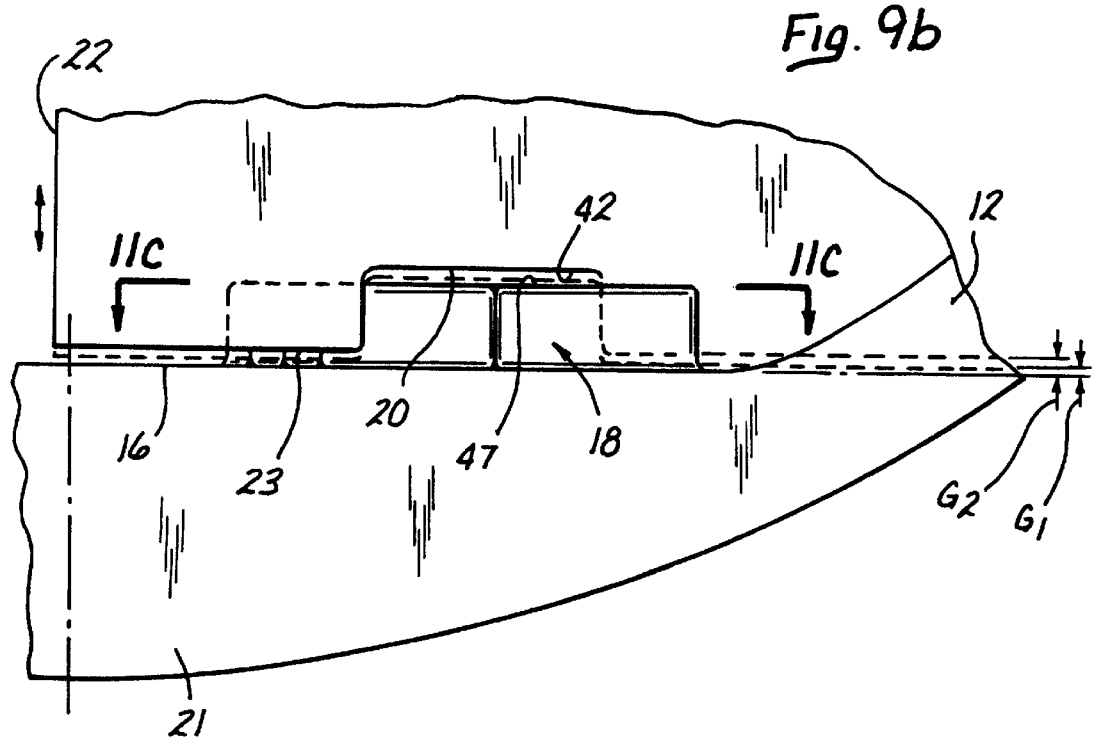
FIG. 9b is a partial elevational view of a bileaflet mechanical cardiovascular valve of the present invention with the occluder leaflet in its fully closed position.
Figure 10:
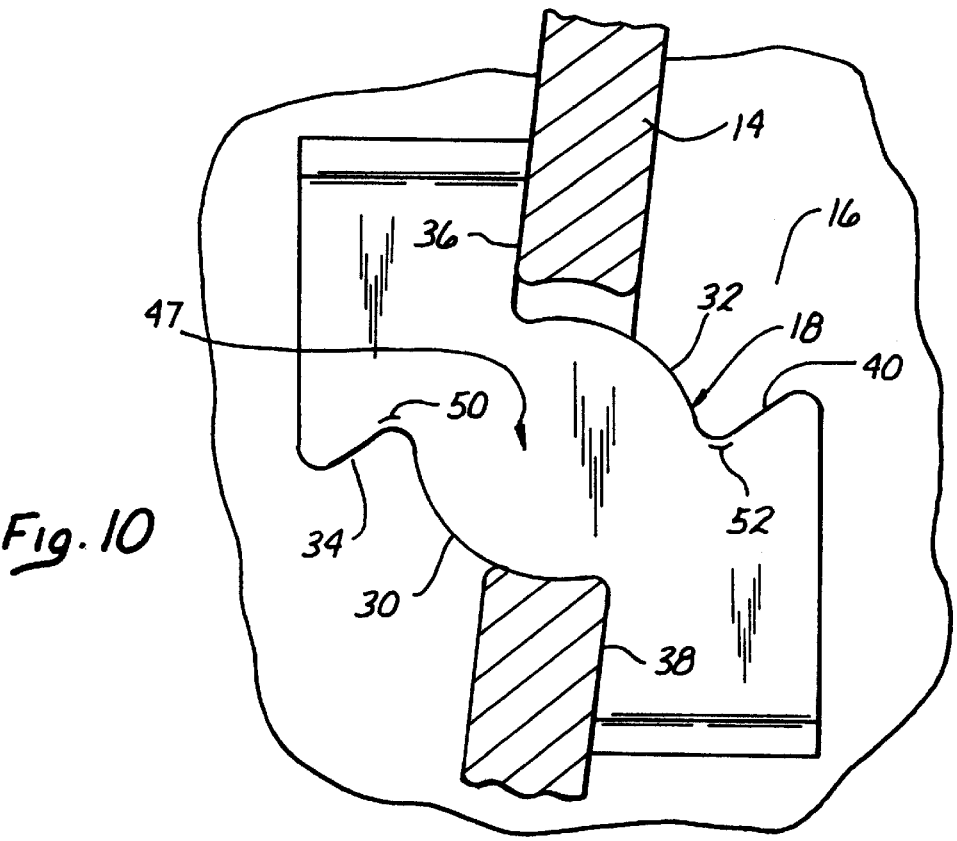
FIG. 10 is a partial sectional view of a portion of a bileaflet cardiovascular valve of the present invention showing the occluder leaflet positioned in a fully open position.

The leaflets 14 are preferably sized such that they may float up and down, between the above-described upper float limit and lower float limit, without causing the flat end edges 23 of the leaflets 14 to come into contact with the upper and lower flat surfaces 16 of the annular valve body 12. In this regard, the flat end edges 23 of the leaflets 14 are prevented from contacting the opposing flat surfaces 16 of the annular valve body 12, thereby minimizing frictional drag as the leaflets 14 move between their opened and closed positions. Additionally, the lack of abutting contact between the flat end edges 23 of the leaflets 14 and the opposing flat surfaces 16 of the annular valve body provides for a gap $G_1$–$G_2$ therebetween. As shown in FIG. 9b, the width of this gap $G_1$–$G_2$ between the flat end edges 23 of the leaflets 14 and the opposing flat surfaces 16 of the annular valve body 12 may vary between a maximum width $G_2$ and a minimum width $G_1$, as the leaflets freely float up and down between their upward float limit and downward float limit, as described hereabove. In the preferred embodiment such gap $G_1$–$G_2$ will typically vary between a maximum $G_2$ of approximately 0.014 inches and a minimum $G_1$ of approximately 0.002 inches. When the leaflets 14 are in their closed positions, blood will seep through the gaps $G_1$–$G_2$ which exist between the flat end edges 23 of the leaflets 14 and the opposing flat areas 16 of the annular valve body, thereby preventing blood from stagnating, or becoming adherent to, the flat end edges 23 of the leaflets 14 and the opposing flat surfaces 16 of the annular valve body 12.

Also, when the leaflets 14 are in their closed positions, a space 50, 52 will exist between the first flanking abutment surfaces 34, 40 of the mounting members 18 and the respective front and rear surfaces FS, RS of the leaflet 14 which abut thereagainst. Thus, blood which seeps between the flat end edges 23 of the leaflets and the flat surfaces 16 of the valve body will subsequently pass through the spaces 50, 52 between the front and rear surfaces FS, RS of the leaflet 14 and the first flanking abutment surfaces 34, 40 of the leaflet mounting member 18. This promotes a further clearing of stagnating or adherent blood which may tend to lodge between first and second flanking abutment surfaces 34, 40 and the adjacent front and rear surfaces FS, RS, of the leaflets 14.

To facilitate the desired upward and downward floating of the leaflets 14, and the desired provision of gaps between the flat end edges 23 of the leaflets and the opposing flat areas 16 of the annular valve body 12, it is necessary that certain relative dimensions of the leaflets 14 and annular valve body 12 be maintained. With reference to the dimensions labeled on FIGS. 5b and 7, the following dimensional definitions and ranges are preferred:

$H_1$ is the linear distance or height between the flat end edges 23 at the upper and lower ends of each leaflet 14.

$H_2$ is the linear distance or height of between the opposing flat area 16 formed on the inner surface of the annular valve body 12.

$H_3$ is the linear distance or height between the flat inner surfaces 42 of the slots 20 formed at opposite ends of a leaflet 14.

$H_4$ is the linear distance or height $H_4$ between the flat top surfaces 47 of directly opposing leaflet mounting members 18 formed opposite one another on the annular valve body 12.

The difference between $H_1$ and $H_2$ is preferably in the range of 0.005–0.023 inches;

The difference between $H_3$ and $H_4$ is preferably in the range of 0.001–0.0045 inches; and, The resultant gap width between the flat end edges 23 of the leaflets 14 and the adjacent flat area 16 of the annular valve body 12 will vary between a minimum gap width $G_1$ of at least 0.002 inches and a maximum gap width $G_2$ of no greater than 0.014 inches.

Additionally, the components of the valve 10 are specifically sized and configured to minimize the obstruction to blood flow through the blood passageway of the annular valve body 12, and to prevent any unnecessary disturbance of such blood flow. In particular, the leaflet mounting members 18 are constructed such that the peripheral or generally rectangular end portions of the mounting members 18 (i.e., the portions which form the first and second flanking abutment surfaces 34, 36, 38, 40) are no greater in height than the central body portion (i.e., the portion which forms the first and second generally arcuate surface, 30, 32) thereof. Preferably, the flat top surface 47 of each leaflet mounting member 18 is a flat smooth surface and the height of each mounting member 18 (i.e., the linear distance from the flat top surface 47 of the mounting member 18 to the flat area 16 of the annular valve body 12 upon which that mounting member 18 is formed) is constant, and is within the range of 0.025–0.030 inches. Additionally, the corners of the mounting members 18 which transition from the vertical edge surfaces thereof to the flat top surface 47 thereof are rounded so as to promote smooth non-turbulent blood flow thereover.

Because the end portions of the leaflet mounting members 18 are no greater in height than the central body portion thereof, the obstruction to blood flow which is created by the exposed end portions of the leaflet mounting members 18 when the leaflet 14 are in their open positions (FIG. 1b) is minimized. Preferably, the mounting members 18 are oriented in the passageway of the annular valve body 12 so that one of the end portions extends generally in the backflow direction and the other end portion extends generally in the outflow direction, and the end portions of each mounting member 18 have a generally arrowhead shape.

Thus, the above-described specific configurations and sizings of the valve leaflets 14 and annular valve body 12 result in reproducible pivotal movement of the leaflets 14 between their open and closed positions, with minimal surface-to-surface impact and minimal obstruction to blood flow to blood passageway of the annular valve body 12. The preferred movement and articulation of the valve leaflets 14 relative to the annular valve body 12 is described in detail here below.

E. Movement of the Leaflets

FIGS. 11a–11e and 11a'–11e' show, in step-by-step fashion, the manner in which a leaflet slot 20 articulates in relation to the mounting member 18 upon which it is mounted.

Figure 11A:
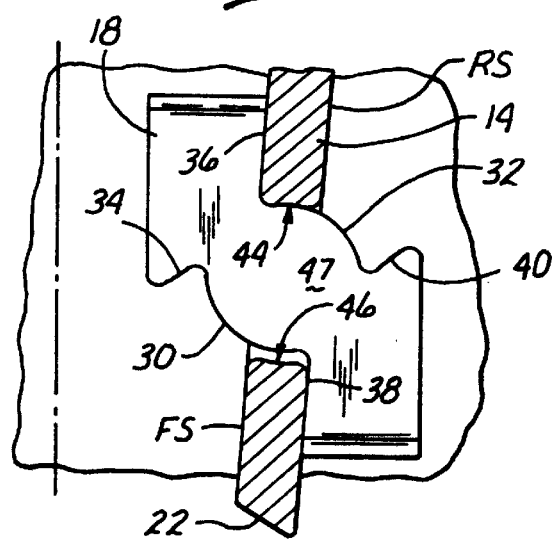
FIGS. 11a–11e and 11a'–11e' are step-wise illustrations of the manner in which the occluder leaflets of a bileaflet mechanical cardiovascular valve of the present invention move between their open and closed positions.
Figure 11A:
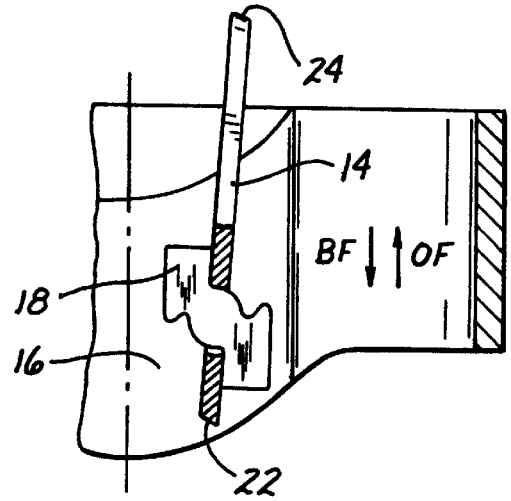
Figure 11B:
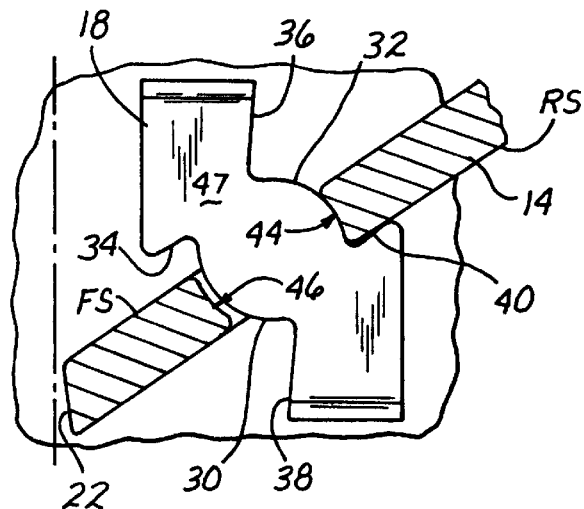
Figure 11B:
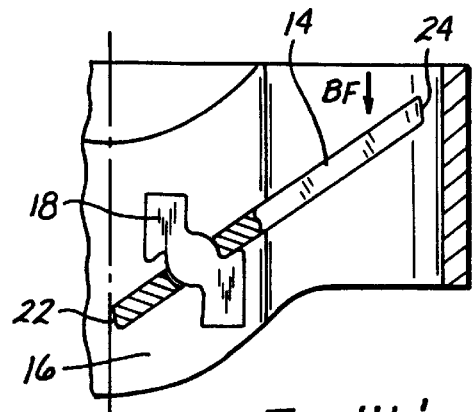

FIGS. 11a and 11a' show the position of the slot 20 relative to the mounting member 18 at that point in the hemodynamic cycle when the flow of blood in the outflow direction OF has ceased, and reverse flow of blood in the backflow direction BF has just begun. The front surface FS of the occluder leaflet is in abutment with the first flanking abutment surface 36 of the mounting member 18. The rear surface RS of the leaflet 14 is in abutment with the first flanking abutment surface 38. In response to the hemodynamic pressure in the backflow direction BF, the leaflet 14 has transitioned in the backflow direction BF such that the second radially curved end 44 of the slot 20 is in abutment with the second generally arcuate surface 32 of the mounting member 18 and the first radially curved end 46 of the slot 20 is spaced away from the first generally arcuate surface 30 of the mounting member 18.

Thereafter, as the hemodynamic force of the blood remains in the backflow direction BF, the occluder leaflets 14 will move from their fully open positions (FIGS. 11a and 11a') to transitionally closed positions (FIGS. 11b and 11b') whereby the first radially curved end 44 of the slot 20 rides along the second arcuate surface 32 until the rear surface RS of the occluder leaflet 14 abuts against the second abutment surface 40 at the second end of the second generally arcuate surface 32. When the occluder leaflet 14 is in this transitional closing position, the second radially curved end 46 of slot 20 remains a spaced distance away from the first generally arcuate surface 30 of the leaflet mounting member 18, and the front surface FS of the occluder leaflet remains a spaced distance away from the second flanking abutment surface 34 at the second end of the first generally arcuate surface 30.

Figure 11C:
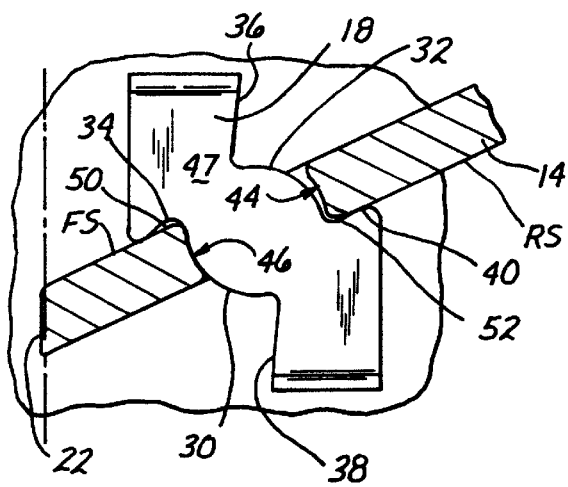
Figure 11C:
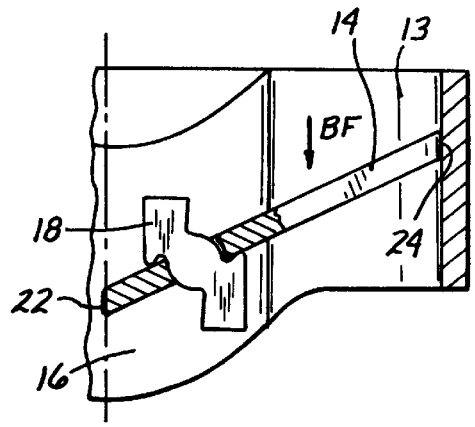

Thereafter, the occluder leaflet 14 moves from its transitional closing position (FIGS. 11b and 11b') to its fully closed position (FIGS. 11c and 11c'). In this phase of the closing movement of the leaflet 14, the hemodynamic force of the blood flow against the front surface FS of the occluder leaflet 14 causes the occluder leaflet 14 to further shift to a position, as shown in FIG. 11c, wherein the front surface FS of the occluder leaflet 14 is in abutment with the second flanking abutment surface 34 at the second end of the first generally arcuate surface 30 of the leaflet mounting member 18, the second radially curved end 46 of the slot 20 is in contact with the first generally arcuate surface 30 of the leaflet mounting member 18, the second radially curved end 44 of the slot 20 has partially separated away from the second generally arcuate surface 32 of the leaflet mounting member 18, and the rear surface RS of the occluder leaflet 14 remains in contact with the second flanking abutment surface 40 at the second end of the second generally arcuate surface 32. As shown in FIG. 11c', each occluder leaflet 14 is free to move to its fully closed position independently of the other and, in the event that one occluder leaflet reaches its fully closed position (FIGS. 11c and 11c') prior to the other, the inner edge 22 of the first-closing occluder leaflet 14 will protrude slightly over the midline (phantom line on FIG. 11c') of the annular valve body. Thereafter, as the other occluder leaflet 14 reaches its fully closed position, the inner edges 22 of the occluder leaflets 14 will come into abutment with one another, and the outer edges 24 of the occluder leaflets will be in abutment with the arcuate inner surface 13 of the annular valve body 12, as shown in FIG. 11c'. When in such fully closed positions (FIGS. 11c and 11c') the front surfaces FS of the leaflets 14 form an angle of 120°–140°.

Figure 11D:
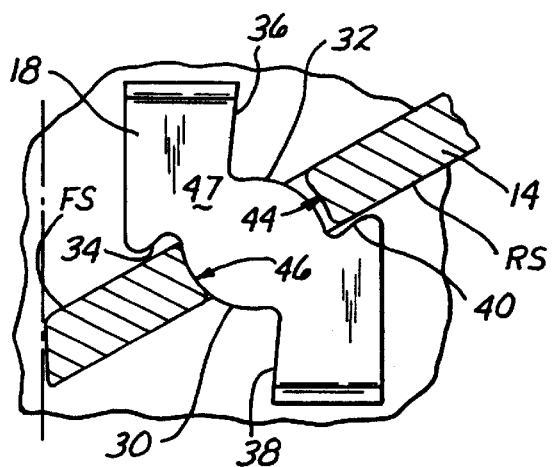
Figure 11D:
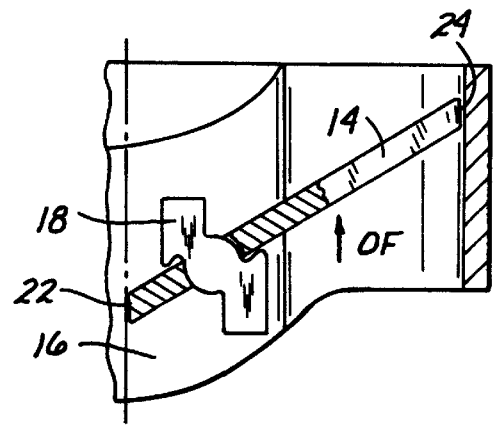

As the hemodynamic direction of blood flow changes to the outflow of direction OF, the occluder leaflet 14 will to move from its fully closed position (FIGS. 11c and 11c') through a transitional opening position shown in FIG. 11d. While in such transitional opening position, the second radially curved end 46 of slot 20 is in contact with, and rides against, the first generally arcuate surface 30 of the leaflet mounting member 18, and the first radially curved end 44 of slot 20 remains a spaced distance away from the second generally arcuate surface 32 of the leaflet mounting member 18. The rear surface RS of the occluder leaflet 14 departs from contact with the second flanking abutment surface 40 at the second end of the second generally arcuate surface 32, and the front surface FS of the occluder leaflet 14 departs from abutment with the second flanking abutment surface 34 at the second end of the first generally arcuate surface 30. In this regard, the occluder leaflet undergoes pivotal movement towards its fully open position, with the first radiused end 46 of the slot 20 riding against the first generally arcuate surface 30 of the leaflet mounting member 18. As shown in corresponding FIG. 11d', the arcuate outer surface 24 of the occluder leaflet 14 will thereby depart from its contact with the inner surface 13 of the annular valve body 12, and the inner edge 22 of the occluder leaflet 14 will depart from its abutting contact with the inner edge 22 of the other occluder leaflet 14, and will move away from the midline (phantom lines) on FIGS. 11a'–11e') of the annular valve body 12.

Figure 11E:
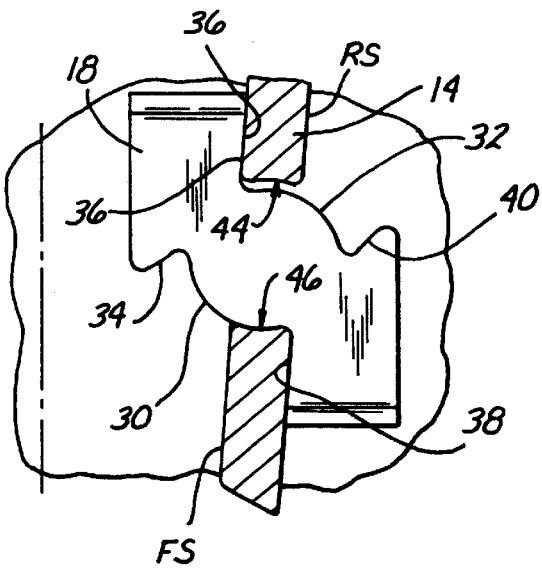
Figure 11E:
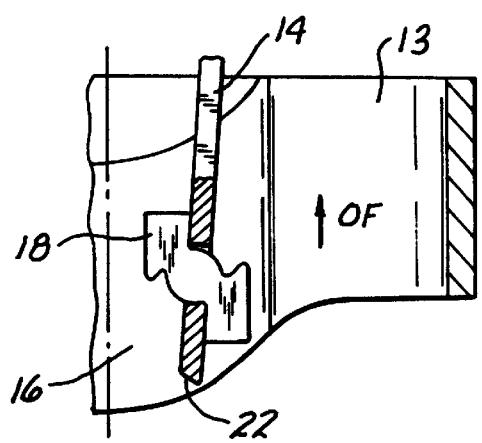

Thereafter, the occluder leaflet 14 continues such pivotal movement until it reaches a fully open position, as shown in FIG. 11e. When in such fully open position (FIGS. 11e and 11e') the second radially curved end 46 of the slot remains in abutment with the first generally arcuate surface, the second radially curved end 44 of the slot 20 remains a spaced distance away from the second generally arcuate surface 32, the rear surface RS of the occluder leaflet is in contact with the first flanking abutment surface 38 at the first end of the first generally arcuate surface 30, and the front surface FS of the occluder leaflet 14 is in abutment with the first flanking abutment surface 36 at the first end of the second generally arcuate surface 32. When in their fully closed positions the rear surfaces RS of the leaflets form an angle of 6°–16° relative to one another.

Thereafter, when the direction of blood flow again changes from the outflow OF direction to the backflow BF direction, each occluder leaflet 14 will shift from the fully open position (FIGS. 11e and 11e') wherein the second radially curved end 46 of the slot 20 is in abutment with the first generally arcuate surface 30 of the leaflet mounting member 18, to the position shown in FIGS. 11a and 11a' wherein the first radially curved end 44 is in abutment with the second generally arcuate surface 32 of the leaflet mounting member 18, and the second radially curved end 46 of the slot has moved a spaced distance away from the first generally arcuate surface 30. Thereafter, the leaflets 14 will repeat the closing and opening movements described hereabove.

Thus, as described hereabove, each occluder leaflet 14 repeatedly moves back and forth between an open position (FIGS. 11a, 11e) wherein blood is permitted to flow in the outflow direction OF through the annular valve body 12, and a closed position (FIG. 11c) wherein the occluder leaflets 14 prevent blood from flowing in the backflow direction BF through the annular valve body 12.

F. Preferred Methods and materials for Construction of the Valve

The annular valve body 12 and occluder leaflets 14 may be formed of any suitable material including, but not necessarily limited to, titanium, titanium alloys, zirconium, and pyrolytic carbon deposited upon a graphite substrate. The occluder leaflets may be formed of any suitable material including, but not necessarily limited to, titanium, titanium alloys, and pyrolytic carbon deposited upon a graphite substrate.

The annular valve body 12 and/or occluder leaflets 14 may be formed or manufactured by any suitable means. Examples of means by which the annular valve body 12 and/or occluder leaflets 14 may be formed include electron discharge machining (EDM) and die casting.

It will be appreciated that the invention has been described herein with reference to certain presently preferred embodiments of the invention, and that various additions, deletions, alterations and modifications may be made to the herein described embodiments without departing from the intended spirit and scope if the invention. It is intended that all such additions, deletions, modifications and alterations be included within the scope of the following claims.

What is claimed is:

1. A bileaflet cardiovascular valve comprising:

an annular valve body having an inner surface which defines a central blood flow passageway extending therethrough;

a first pair of leaflet mounting members formed at a first location on the inner surface of said annular valve body and a second pair of leaflet mounting members formed at a second location on the inner surface of said annular valve body, said second location being directly opposite said first location;

each of said mounting members comprising a raised mass protruding from the inner surface of said annular valve body, each of said mounting members having a central body portion with opposed edge surfaces, each mounting member including first and second end portions located adjacent opposite ends of and extending outward from said central body portion to each form a first flanking abutment surface adjacent one of said edge surfaces and a second flanking abutment surface adjacent the other of said edge surfaces;

first and second occluder leaflets having slots formed therein, the slots of said occluder leaflets being mounted upon the central body portions of said leaflet mounting members such that said leaflets may pivot thereon between:

i. a closed position where said leaflets block blood flow through the blood flow passageway in at least a backflow direction; and, ii. an open position wherein said leaflets permit blood to flow through said blood flow passageway in at least an outflow direction;

wherein said mounting members are oriented with said first end portion extending generally in the backflow direction and each of said end portions has a generally arrowhead shape.

2. The valve of claim 1 wherein:

first and second flat areas are formed at directly opposite locations on the inner surface of said annular valve body; and, said first pair of leaflet mounting members are formed on the first flat area on the inner surface of said annular valve body and said second pair of leaflet mounting members are formed on the second flat area on the inner surface of said annular valve body; and, the first and second end portions and central body portions of each leaflet mounting member are equal in height, and each leaflet mounting member has a substantially flat upper surface which is disposed at a constant height above the respective one of said flat areas upon which that mounting member is positioned.

3. The valve of claim 1, wherein the raised mass of each mounting member has a first convex surface on one side thereof and a second convex surface on an opposite side thereof.

4. The valve of claim 3 wherein each of said slots is a cut out area formed in the leaflet with radially curved ends which reside next to the generally convex surfaces of the central body portions of the mounting members.

5. The valve of claim 3 wherein the first convex surface of the central body portion of each leaflet mounting member includes a first convex segment having a first radius and a first center point and a second convex segment having a second radius and a second center point different from said first radius and said first center point.

6. The valve of claim 3 wherein the first generally convex surface of the central body portion of each leaflet mounting member includes a first convex segment having a first radius and a first center point and a second convex segment having a second radius and a second center point, said first and second radii being of different length, and said first and second center points being at different locations.

7. The valve of claim 1, wherein at least one of the said first and second flanking abutment surfaces is straight.

8. The valve of claim 1 wherein said annular valve body is devoid of protrusions extending into said central blood flow passageway from the inner surface of said annular valve body, except for said pairs of leaflet mounting members, to further minimize obstructions to the flow of blood when the valve is open.

9. The device of claim 1 wherein said second flanking abutment surface is of curved configuration such that, when a front surface of the occluder leaflet is in abutment with said second flanking abutment surface, a space will exist therebetween to permit seepage of blood therethrough.

10. The valve of claim 1 wherein the first and second end portions are no greater in height than the central body portion thereof.

11. A self-washing bileaflet mechanical cardiovascular valve which substantially occludes blood flow in a closed state while allowing some seepage between the leaflets and pivot members to facilitate clearance of stagnating or adherent blood, comprising:

an annular valve body having an inner surface and a central blood flow passageway extending therethrough;

first and second pairs of leaflet pivot members formed at opposite locations on the inner surface of said annular valve body;

each of said leaflet pivot members extending into the blood flow passageway and having a central body portion with opposed edge surfaces, each pivot member including first and second end portions located adjacent opposite ends of and extending outward from said central body portion to each form a first flanking abutment surface adjacent one of said edge surfaces and a second flanking abutment surface adjacent the other of said edge surfaces;

first and second occluder leaflets, each of said occluder leaflets having a front surface, a rear surface, a generally straight inner edge, a generally arcuate outer edge and first and second end edges;

slots formed in the first and second end edges of each occluder leaflet, each of said slots being configured to receive therein the central body portion of a leaflet pivot member so that the slot in the first end edge of each of said leaflets cooperates with one of the first pair of pivot members, and the slot in the second end edge of each of said leaflets cooperates with one of the second pair of pivot members;

said leaflets being pivotally moveable between:

i. a closed position with said front surface and said second flanking abutment surfaces being shaped to together define first blood flow seepage spaces therebetween, and said rear surface contacting the second flanking abutment surfaces adjacent said second edge surfaces on both cooperating pivot members, said rear surface and said second flanking abutment surfaces being shaped to together define second blood flow seepage spaces therebetween, wherein the generally straight inner edges of said occluder leaflets are in abutment with one another and the generally arcuate outer edges of said occluder leaflets are in abutment with the inner surface of said annular valve body thereby substantially blocking blood flow in a first direction through the blood flow passageway of said annular valve body; and ii. an open position wherein said leaflets are substantially parallel to one another, thereby allowing blood to flow through the blood flow passageway of the annular valve body in a second direction opposite said first direction; and wherein portions of the front and rear surfaces of the leaflets which abut against the cooperating second flanking abutment surfaces of the pivot members in the closed positions of the leaflets are flat, and said second flanking abutment surfaces include indentations which, in conjunction with the flat portions, form said seepage spaces.

12. The valve of claim 11 wherein each said leaflets has a size forming a gap between first and second end edges thereof and the annular valve body and floats back and forth within limits defined by contact between its two slots and the central body portions on the cooperating pivot members on each side of the annular valve body.

13. The valve of claim 12 wherein said gaps formed between the first and second end edges and the annular valve body are sized between approximately 0.002 inches and 0.014 inches.

14. The valve of claim 11 wherein the second flanking abutment surfaces are curved, and, in conjunction with said flat portions of the front and rear surfaces of the leaflets, form said seepage spaces.

15. A self-washing bileaflet mechanical cardiovascular valve which substantially occludes blood flow in a closed state while allowing some seepage between the leaflets and pivot members to facilitate clearance of stagnating or adherent blood, comprising:

an annular valve body having an inner surface and a central blood flow passageway extending therethrough;

first and second pairs of leaflet pivot members formed at opposite locations on the inner surface of said annular valve body;

each of said leaflet pivot members extending into the blood flow passageway and having a central body portion with opposed edge surfaces, each pivot member including first and second end portions located adjacent opposite ends of and extending outward from said central body portion to each form a first flanking abutment surface adjacent one of said edge surfaces and a second flanking abutment surface adjacent the other of said edge surfaces;

first and second occluder leaflets, each of said occluder leaflets having a front surface, a rear surface, a generally straight inner edge, a generally arcuate outer edge and first and second end edges;

slots formed in the first and second end edges of each occluder leaflet, each of said slots being configured to receive therein the central body portion of a leaflet pivot member so that the slot in the first end edge of each of said leaflets cooperates with one of the first pair of pivot members, and the slot in the second end edge of each of said leaflets cooperates with one of the second pair of pivot members;

said leaflets being pivotally moveable between:

i. a closed position with said front surface and said second flanking abutment surfaces being shaped to together define first blood flow seepage spaces therebetween, and said rear surface contacting the second flanking abutment surfaces adjacent said second edge surfaces on both cooperating pivot members, said rear surface and said second flanking abutment surfaces being shaped to together define second blood flow seepage spaces therebetween, wherein the generally straight inner edges of said occluder leaflets are in abutment with one another and the generally arcuate outer edges of said occluder leaflets are in abutment with the inner surface of said annular valve body thereby substantially blocking blood flow in a first direction through the blood flow passageway of said annular valve body; and ii. an open position wherein said leaflets are substantially parallel to one another, thereby allowing blood to flow through the blood flow passageway of the annular valve body in a second direction opposite said first direction;

wherein said front and rear surfaces of said leaflets and said second flanking abutment surfaces are shaped to together define blood flow seepage spaces therebetween while said leaflets are in their closed positions; and wherein portions of said front and rear surfaces of said leaflets which contact said second flanking abutment surfaces are flat and said second flanking abutment surfaces are concavely curved away from said flat portions to form said seepage spaces.

16. The valve of claim 15, wherein the central body portion of each pivot member has opposed generally convex upstream and downstream edge surfaces, and wherein each of said slots is a cut out area formed in the leaflet with radially curved upstream and downstream ends adjacent said generally convex edge surfaces of the central body portion of the cooperating pivot member.

17. The valve of claim 15, wherein the central body portion of each pivot member has opposed generally convex upstream and downstream edge surfaces, and wherein the upstream and downstream convex edge surfaces of the central body portion of each pivot member include segments having different radii of curvature.

18. The valve of claim 15, wherein the central body portion of each pivot member has opposed generally convex upstream and downstream edge surfaces, and wherein the upstream and downstream edge surfaces on each pivot member each include a first segment diametrically opposed across said central body portion and a second segment diametrically opposed across said central body portion, said first segments being adjacent said first flanking abutment surfaces and having larger radii of curvature than said second segments.

19. The valve of claim 15, wherein said second flanking abutment surfaces are curved.

20. The valve of claim 19, wherein said first flanking abutment surfaces are straight.

21. A bileaflet mechanical cardiovascular valve comprising:

an annular valve body having an inner surface and a central blood flow passageway extending therethrough;

first and second pairs of leaflet mounting members formed at opposite locations on the inner surface of said annular valve body, each of said leaflet mounting members comprising a raised member having a central body portion with opposed edge surfaces, each mounting member including first and second arrowhead-shaped end portions located adjacent opposite ends of and extending outward from said central body portion, each end portion being partially defined by a first flanking abutment surface adjacent one of said edge surfaces and a second curved flanking abutment surface adjacent the other of said edge surfaces, said curved second flanking abutment surfaces on the end portions of any one of said pivot members being adjacent opposite edge surfaces on said one pivot member so as to face in the same rotational direction about said central body portion;

first and second generally flat occluder leaflets, each of said occluder leaflets having a front surface, a rear surface, a generally straight inner edge, a generally arcuate outer edge and first and second end edges;

slots formed in the first and second end edges of each occluder leaflet, each of said slots being configured to receive therein the central body portion of a cooperating leaflet mounting member, each of said leaflets being mounted within the annular valve body with both said slots being positioned over the central body portions of the cooperating leaflet mounting members and being thereby pivotally moveable between positions limited by contact between said front and rear surfaces and said flanking abutment surfaces on the cooperating mounting members, each said leaflet being pivotable into at least a closed position wherein the generally straight inner edges of said occluder leaflets are in abutment with one another and the generally arcuate outer edges of said occluder leaflets are in abutment with the inner surface of said annular valve body thereby blocking blood flow in at least a first direction through the blood flow passageway of said annular valve body, and wherein said front and rear surfaces contact the curved second flanking abutment surfaces adjacent said edge surfaces on both cooperating mounting members to define blood flow seepage spaces therebetween.

22. The valve of claim 21 wherein said edge surfaces of the central body portion of each mounting member are generally convex.

23. The valve of claim 22 wherein each of said slots is a cut out area formed in the leaflet with radially curved upstream and downstream ends adjacent said generally convex edge surfaces of the central body portion of the cooperating mounting member.

24. A bileaflet mechanical cardiovascular valve comprising:

an annular valve body having an inner surface and a central blood flow passageway extending therethrough;

first and second pairs of leaflet mounting members formed at opposite locations on the inner surface of said annular valve body, each of said leaflet mounting members comprising:

i. a central body portion comprising a raised member having a first generally convex surface on one side thereof and a second generally convex surface on an opposite side thereof, said first and second generally convex surfaces having first and second ends;

ii. a first flanking abutment surface formed adjacent to the first end of each of said first and second generally convex surfaces;

iii. a second flanking abutment surface formed adjacent the second end of each of said first and second generally convex surfaces;

first and second occluder leaflets, each of said occluder leaflets having a front surface, a rear surface, a generally straight inner edge, a generally arcuate outer edge and first and second end edges;

slots formed in the first and second end edges of each occluder leaflet, each of said slots being configured to receive therein the central body portion of a leaflet mounting member;

said leaflets being mounted within the annular valve body with said slots being positioned over the central body portions of the leaflet mounting members, said leaflets being thereby pivotally moveable between:

i. a closed position wherein the generally straight inner edges of said occluder leaflets are in abutment with one another and the generally arcuate outer edges of said occluder leaflets are in abutment with the inner surface of said annular valve body thereby blocking blood flow, in at least a first direction, through the blood flow passageway of said annular valve body; and ii. an open position wherein said leaflets are substantially parallel to one another, thereby allowing blood to flow through the blood flow passageway of the annular valve body, in at least a second direction;

wherein said first flanking abutment surfaces of each leaflet mounting member are straight and said second flanking abutment surfaces of each leaflet mounting member are curved.

25. The valve of claim 24 wherein each of said slots is a cut out area formed in the leaflet with radially curved ends which reside next to the generally convex surfaces of the central body portions of the mounting members.

26. The valve of claim 24 wherein:

said occluder leaflets are configured such that, when in their closed position the front surface of each occluder leaflet is in abutment with the second flanking abutment surface at the second end of the first generally convex surface of the leaflet mounting member and the rear surface of each occluder leaflet is in abutment with the second flanking abutment surface at the second end of the second generally convex surface of each leaflet mounting member.

27. The device of claim 26 wherein said second flanking abutment surfaces are of curved configuration such that, when the front surface of the occluder leaflet is in abutment with said second flanking abutment surface, a space will exist therebetween to permit seepage of blood therethrough.

28. The valve of claim 24 wherein the portions of the rear surfaces of the leaflets which abut against the second flanking abutment surfaces of the mounting members are flat, such that some gap exists between the curved second flanking abutment surfaces and the portions of the rear surfaces of the leaflets which abut thereagainst, said gap providing a passageway through which blood may seep while said leaflets are in their closed positions.

29. The valve of claim 24 wherein said occluder leaflets are configured such that, when in their open positions, the rear surface of each occluder leaflet will be in abutment with the first flanking abutment surface at the first end of the first generally convex surface of the leaflet mounting member and the front surface of the occluder leaflet will be in abutment with the first flanking abutment surface at the first end of the second generally convex surface of the leaflet mounting member.

30. The valve of claim 24 wherein flat areas are formed on the inner surface of the annular valve body, on opposite sides thereof, and wherein said leaflet mounting members are located on said flat areas.

31. The valve of claim 30 wherein said occluder leaflets are mounted within said annular valve body such that said occluder leaflets may float back and forth between the opposing flat areas formed on the inner surface of the annular valve body.

32. The valve of claim 31 wherein said occluder leaflets are sized, relative to said annular valve body, such that said occluder leaflets will float between limit points whereat said slots formed in the first and second end edges of said occluder leaflets become bottomed out against the leaflet mounting members upon which said slots are positioned, but even when one of said slots is bottomed out against the mounting member upon which that slot is positioned, the flat end edge of the leaflet in which that slot is formed will not contact the adjacent flat area on the inner surface of the annular valve body.

33. The valve of claim 32 wherein a gap will remain between the end edge of each occluder leaflet and the adjacent flat area of the annular valve body as said occluder leaflets float within said annular valve body, each of said gaps varying between a minimum gap width of at least 0.002 inches and a maximum gap width of no greater than 0.014 inches.

34. The valve of claim 24 wherein said annular valve body is formed of material selected from the group of materials consisting of:
   a) titanium;
   b) titanium alloys;
   c) zirconium; and,
   d) graphite coated with pyrolytically deposited carbon.

35. The valve of claim 24 wherein the occluder leaflets are formed of material selected from the group of materials consisting of:
   a) titanium;
   b) titanium alloys; and,
   c) graphite coated with pyrolytically deposited carbon.

36. The valve of claim 24 wherein the first convex surface of the central body portion of each leaflet mounting member includes a first convex segment having a first radius and a first center point and a second convex segment having a second radius and a second center point different from said first radius and said first center point.

37. The valve of claim 24 wherein the first generally convex surface of the central body portion of each leaflet mounting member includes a first convex segment having a first radius and a first center point and a second convex segment having a second radius and a second center point, said first and second radii being of different length, and said first and second center points being at different locations.

38. The valve of claim 25 wherein the center to center distance between the radially curved ends of each slot is 0.010–0.017 inches greater than the distance between the first and second generally convex surfaces of the central body portion of the leaflet mounting member upon which the slot is mounted, thereby allowing 0.010–0.017 inches of longitudinal play of said leaflet relative to the central body portion of the leaflet mounting member.

39. The valve of claim 24 wherein said leaflet mounting members are formed on the inner surface of said annular valve body by electron discharge milling.

40. The valve of claim 24 wherein said leaflet mounting members are formed on the inner surface of said annular valve body by die casting.

41. The valve of claim 24 wherein said leaflet mounting members are positioned on said annular valve body, and wherein said occluder leaflets are sized and configured, such that when said occluder leaflets are in their closed positions, the front surfaces of said occluder leaflets form an angle of 120°–140° degrees relative to one another.

42. The valve of claim 24 wherein said leaflet mounting members are positioned on said annular valve body, and wherein said occluder leaflets are sized and configured, such that when said occluder leaflets are in their open positions, the rear surfaces of said occluder leaflets form an angle of 6°–16° degrees relative to one another.

43. The valve of claim 24 the first and second ends of said first and second convex surfaces are no greater in height than the central body portion thereof.

44. A bileaflet mechanical cardiovascular valve comprising:
   an annular valve body having an inner surface and a central blood flow passageway extending therethrough;
   first and second pairs of leaflet mounting members formed at opposite locations on the inner surface of said annular valve body, each of said leaflet mounting members comprising:
      i. a central body portion comprising a raised member having a first generally convex surface on one side thereof and a second generally convex surface on an opposite side thereof, said first and second generally convex surfaces having first and second ends;
      ii. a first flanking abutment surface formed adjacent to the first end of each of said first and second generally convex surfaces;
      iii. a second flanking abutment surface formed adjacent the second end of each of said first and second generally convex surfaces;
   first and second occluder leaflets, each of said occluder leaflets having a front surface, a rear surface, a generally straight inner edge, a generally arcuate outer edge and first and second end edges;
   slots formed in the first and second end edges of each occluder leaflet, each of said slots being configured to receive therein the central body portion of a leaflet mounting member;
   said leaflets being mounted within the annular valve body with said slots being positioned over the central body portions of the leaflet mounting member, said leaflets being thereby pivotally moveable between:
      i. a closed position wherein the generally straight inner edges of said occluder leaflets are in abutment with one another and the generally arcuate outer edges of said occluder leaflets are in abutment with the inner surface of said annular valve body thereby blocking blood flow, in at least a first direction, through the blood flow passageway of said annular valve body; and
      ii. an open position wherein said leaflets are substantially parallel to one another, thereby allowing blood to flow through the blood flow passageway of the annular valve body, in at least a second direction;
   wherein the first generally convex surface of the central body portion of each leaflet mounting member includes a first convex segment having a first radius and a first center point and a second convex segment having a second radius and a second center point different from said first radius and said first center point; wherein the first and second flanking abutment surfaces of said leaflet mounting members are no greater in height than the central body portions thereof; and wherein said annular valve body is devoid of protrusions extending into said central blood flow passageway from the inner surface of said annular valve body, except for said pairs of leaflet mounting members.

45. The valve of claim 44 wherein at least one of said first and second flanking abutment surfaces is straight.

46. The valve of claim 44 wherein each of said slots is a cut out area formed in the leaflet with radially curved ends which reside next to the generally convex surfaces of the central body portions of the mounting members.

47. The device of claim 44 wherein said second flanking abutment surfaces are of curved configuration such that, when the occluder leaflets are in their closed positions, the front surface of the occluder leaflet is in abutment with said second flanking abutment surface at the second end of the first generally convex surface of the leaflet mounting member, and a space will exist therebetween to permit seepage of blood therethrough.

* * * * *